United States Patent [19]

Shinohara et al.

[11] Patent Number: 4,831,053
[45] Date of Patent: May 16, 1989

[54] COMPOSITION FOR PROPHYLAXIS AND THERAPY OF HEPATITIS

[75] Inventors: Masanao Shinohara; Hirotsugu Kaise; Yoshimasa Nakano; Taketoshi Izawa; Yasuo Oshiro; Wasei Miyazaki, all of Tokushima, Japan

[73] Assignee: Otsuka Pharmaceutical Co., Ltd., Tokyo, Japan

[21] Appl. No.: 81,581

[22] Filed: Aug. 3, 1987

Related U.S. Application Data

[63] Continuation of Ser. No. 831,375, Feb. 18, 1986, abandoned, continuation of Ser. No. 261,215, filed as PCT JP80/00195 on Aug. 22, 1980, abandoned.

[30] Foreign Application Priority Data

Aug. 22, 1979 [JP] Japan ................................. 54-107627

[51] Int. Cl.$^4$ .............................................. A61K 31/34
[52] U.S. Cl. ....................................... 514/462; 514/892
[58] Field of Search ................................. 514/462, 468

[56] References Cited

U.S. PATENT DOCUMENTS 4,229,466 10/1980 Miyazaki et al. .................... 514/462

FOREIGN PATENT DOCUMENTS 2821403  1/1979  Fed. Rep. of Germany .
3031788  3/1981  Fed. Rep. of Germany .

OTHER PUBLICATIONS

Chemical Abstract 95:81275e.

Primary Examiner—Frederick E. Waddell
Attorney, Agent, or Firm—Sughrue, Mion, Zinn, Macpeak & Seas

[57] ABSTRACT

A prophylactic or therapeutic composition for hepatitis is disclosed comprising a prophylactically or therapeutically effective amount of a sesquiterpene compound represented by the formula (I) or (II)

or a pharmaceutically acceptable salt thereof as an active ingredient, and a pharmaceutically acceptable carrier.

2 Claims, 3 Drawing Sheets

COMPOSITION FOR PROPHYLAXIS AND THERAPY OF HEPATITIS

This is a continuation of application Ser. No. 831,375, filed Feb. 18, 1986, now abandoned which is a continuation of application Ser. No. 261,215 filed as PCT TP 80/00/95 Aug. 22, 1980, now abandoned.

TECHNICAL FIELD

This invention relates to composition for prophylaxis and therapy of hepatitis.

BACKGROUND ART

Sesquiterpene derivatives represented by the formulae (I) and (II)

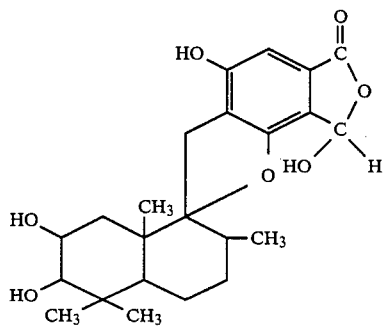

(I)

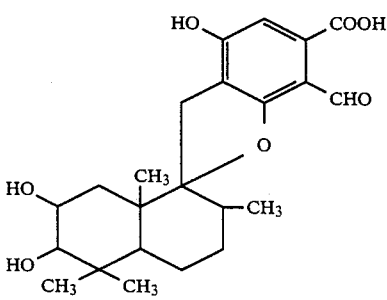

(II)

are known compounds, described in German Patent Application (OLS) No. 2,821,403, and are useful as a therapeutic agent for treating autoimmune disease, nephritis, rheumatism, collagene disease, and cancer.

DISCLOSURE OF INVENTION

After extensive research it has now been found that the compounds represented by the formulae (I) and (II) have therapeutic activity and prophylactic activity with respect to hepatitis which can be unexpected from the utility (pharmacological activity) described in the above-described publication, and are useful as an agent for prophylaxis and treatment of hepatitis.

This invention is based on the above finding and provides a prophylactic and therapeutic agent for hepatitis comprising a prophylactically or therapeutically effective amount of a sesquiterpene derivative represented by the formula (I) or (II)

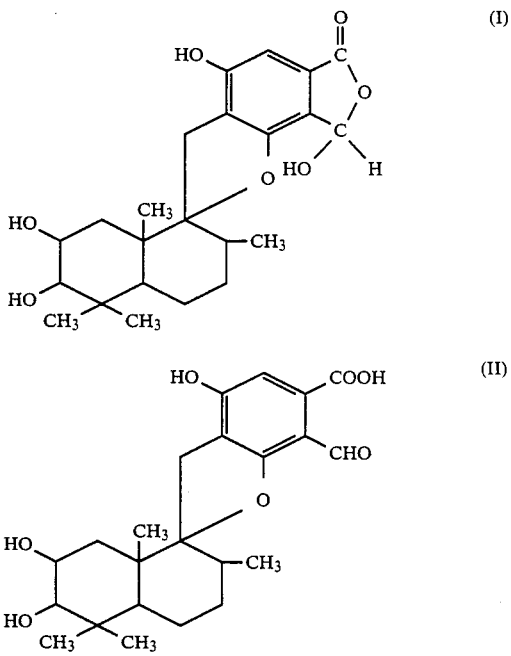

or a pharmaceutically acceptable salt thereof as an active ingredient, and a pharmaceutically acceptable carrier.

In another aspect, this invention provides a method for the prophylaxis or therapy of hepatitis comprising administering to mammals a prophylactically or therapeutically effective amount of a sesquiterpene derivative represented by the formula (I) or (II)

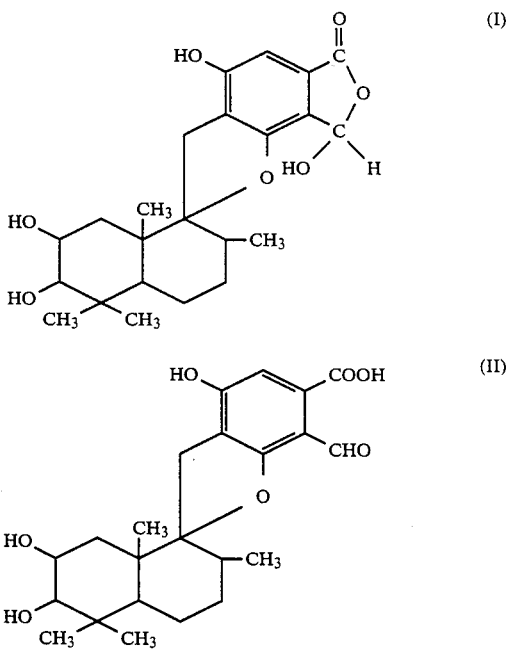

or a pharmaceutically acceptable salt thereof.

BRIEF DESCRIPTION OF INVENTION

BEST MODE FOR CARRYING OUT THE INVENTION

Figure 2:
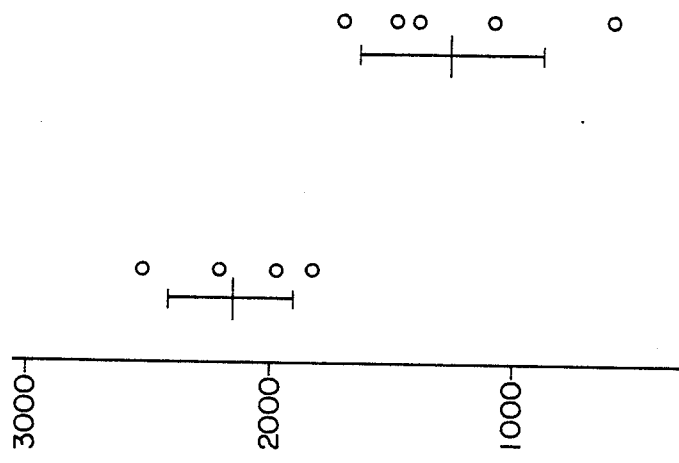
FIG. 2 illustrates lactic dehydrogenase concentrations for control groups and groups treated with the composition of the invention.

In this invention, crystals of the compound represented by the formula (I) form an equilibrium mixture of the compound (I) and monocarboxylic compound represented by the formula (II), which is a tautomer of the compound of formula (I), when the compound of the formula (I) is dissolved in a solvent and particularly in a basic solvent.

More particularly, from nuclear magnetic resonance spectral analysis of the compound represented by the formula (I) dissolved in dimethyl sulfoxide conducted using DSS (sodium 2,2-dimethyl-2-silapentane-5-sulfonate) as an internal standard reagent over a period of time it is found that 20 minutes after the dissolution of compound of formula (I), a peak is observed at 9.89 ppm, corresponding to the characteristic signal of an aldehydic proton (—CHO), in addition to a characteristic signal of a lactole ring at 6.36 ppm. Integration of the areas under the peak signals indicates a proportion of the former to the latter of about 73:27. After 2 hours the peak at 9.89 ppm increase further to an extent that the integrated proportions become about 70:30, and this proportion remains unchanged according to NMR analysis even after 63 hours. From this it follows that the compound represented by formula (I) and that represented by formula (II) are present in a molar proportion of about 7:3 in the solution. However, when methanol or pyridine is used as a solvent, the compound of formula (II) is not formed.

Therefore, the compounds of formulae (I) and (II) can be used as a mixture of tautomers comprising the active ingredient, and reference hereinafter to a compound of formula (I) or (II) is to be understood as including tautomeric mixtures thereof.

The prophylactic or therapeutic agent of this invention can also comprise as an active ingredient a salt of the compound of the formula (I) or (II) with a basic compound. This salt can be prepared by reacting at least one functional group, i.e., an acidic group of the compound represented by the formula (I) or (II), particularly a phenolic hydroxyl group of the compounds represented by the formulae (I) and (II) and carboxyl group of the compound represented by the formula (II) which can lead to formation of a lactole ring, with a basic compound.

Examples of basic compounds that can be used in the production of the salts of the sesquiterpene derivatives of the formula (I) or (II) include the hydroxides and carbonates of alkali metals and alkaline earth metals, such as sodium hydroxide, potassium hydroxide, calcium hydroxide, sodium carbonate, potassium carbonate, and sodium hydrogen carbonate. Organic amines, such as methylamine, ethylamine, isopropylamine, morpholine, piperazine, piperidine, and 3,4-dimethoxyphenethylamine, can also be used as the basic compounds.

The compounds used as active ingredient in the prophylactic and therapeutic agent of this invention have stereoisomers and this invention is to be construed as including the stereoisomers.

Salt formation using basic compounds can be easily conducted in a suitable solvent using conventional salt-formation techniques. Examples of suitable solvents which can be used are water, lower alcohols such as methanol, ethanol and propanol, ethers such as dioxane and tetrahydrofuran, acetone, benzene, ethyl acetate, dimethyl sulfoxide, dimethylformamide, methylene chloride, and chloroform. Salt formation can be carried out at a temperature of from about room temperature to about 100° C., and preferably from room temperature to 50° C., for about 5 minutes to about 6 hours. The salt can usually be formed while the system is open to the atmosphere, or can be conducted under oxygen-free conditions in an atmosphere of an inert gas such as nitrogen or argon. The amount of the basic compound used is not particularly restricted, but usually, a suitable amount is at least about 1 equivalent, and preferably from 1 to 2 equivalents, based on the acidic groups of the starting compound (I) or (II).

After the reactions described above have been completed, the desired final compound can be easily separated and purified using known conventional separation procedures. For example, distillation of solvent, solvent extraction, precipitation, recrystallization, column chromatography, and preparative chromatography can be employed as separation procedures.

The resulting sesquiterpene derivatives of the formula (I) or (II) and the salts thereof of the present invention are useful as agents for prophylaxis and treatment of hepatitis. When used as a hepatitis treating agent, they are formulated into pharmaceutical compositions together with ordinary pharmaceutically acceptable carriers. Suitable carriers which can be used are, for example, diluents or excipients, such as fillers, extenders, binders, wetting agents, disintegrants, surface active agents and lubricants which are usually employed to prepare such drugs depending on the dosage form.

Various dosage forms of the prophylactic or therapeutic agents for hepatitis can be selected according to the purpose of the prophylaxis or therapy. Typical dosage forms which can be used are tablets, pills, powders, liquid preparations, suspensions, emulsions, granules, capsules, suppositories, and injectable preparations (solutions, suspensions, etc.).

In molding a pharmaceutical composition containing the sesquiterpene derivative of the formula (I) or (II) or the pharmaceutically acceptable salt thereof as an active ingredient into a tablet form, a wide range of carriers known in the art can be used. Examples of suitable carriers include excipients such as lactose, white sugar, sodium chloride, glucose, urea, starch, calcium carbonate, kaolin, crystalline cellulose and silicic acid; binders such as water, ethanol, propanol, simple syrup, glucose solution, starch solution, gelatin solution, carboxymethyl cellulose, shellac, methyl cellulose, potassium phosphate and polyvinyl pyrrolidone, disintegrants such as dried starch, sodium alginate, agar powder, laminaria powder, sodium hydrogen carbonate, calcium carbonate, sodium lauryl sulfate, stearic acid monoglyceride, starch, and lactose, disintegration inhibitors such as white sugar, stearic acid glyceryl ester, cacao butter and hydrogenated oils, absorption promotors such as quaternary ammonium bases and sodium lauryl sulfate, humectants such as glycerol and starch, adsorbents such as starch, lactose, kaolin, bentonite and colloidal silicic acid, and lubricants such as purified talc, stearic acid salts, boric acid powder, Macrogol (trademark for a polyethylene glycol produced by Shinetsu Chemical Industry Co., Ltd.) and solid polyethylene glycol.

In molding the pharmaceutical composition into a pill form, a wide variety of conventional carriers known in the art can be used. Examples of suitable carriers are excipients such as glucose, lactose, starch, cacao butter, hardened vegetable oils, kaolin and talc, binders such as gum arabic powder, tragacanth powder, gelatin, and ethanol, and disintegrants such as laminaria and agar.

The tablets, if desired, can be coated, and made into sugar-coated tablets, gelatin-coated tablets, enteric-coated tablets, film-coated tablets, or tablets coated with two or more layers.

In molding the pharmaceutical composition into a suppository form, a wide variety of carriers known in the art can be used. Examples of suitable carriers include polyethylene glycol, cacao butter, higher alcohols, esters of higher alcohols, gelatin, and semi-synthetic glycerides.

When the pharmaceutical composition is formulated into an injectable preparation, the resulting solution and suspension are preferably sterilized and rendered isotonic with respect to the blood. In formulating the pharmaceutical composition into the form of a solution or suspension, all diluents customarily used in the art can be used. Examples of suitable diluents are water, ethyl alcohol, propylene glycol, ethoxylated isostearyl alcohol, polyoxylated isostearyl alcohol, polyoxyethylene sorbitol, and sorbitan esters. Sodium chloride, glucose or glycerol may be incorporated into a prophylactic or therapeutic agent for hepatitis in an amount sufficient to prepare isotonic solutions. The prophylactic or therapeutic agent may further contain ordinary dissolving aids, buffers, pain-alleviating agents, and preservatives, and optionally coloring agents, perfumes, flavors, sweeteners, and other drugs.

The amount of the compound of the formula (I) or (II) and the pharmaceutically acceptable salts thereof of this invention used as an active ingredient incorporated in a pharmaceutical composition useful as a hepatitis treating agent or prophylactic agent for hepatitis is not particularly limited, and can vary over a wide range. A suitable prophylactically or therapeutically effective amount of the compound of the formula (I) or (II) and the pharmaceutically acceptable salts thereof in a composition according to this invention is usually from about 1 to 70% by weight, and preferably from 5 to 50% by weight, based on the total weight of the composition.

There is no particular restriction on the manner of using the prophylactic or therapeutic agent for hepatitis and the prophylactic or therapeutic agent can be administered by routes suitable for the particular forms of the agent. For example, the tablets, pills, liquid preparations, suspension, emulsions, granules, and capsules can be orally administered. Injectable preparations can be administered intravenously, intramuscularly, intracutaneously, subcutaneously, or intraperitoneally. Furthermore, the therapeutic agent can be administered either alone or together with ordinary auxiliary agents such as glucose and amino acids. A suppository form would be administered intrarectally.

The dosage of the prophylactic or therapeutic agent for hepatitis is suitably selected according to the purpose of use, the symptoms, etc. Usually, a preferred dosage of the compound of this invention is from about 50 mg to 1 g per day (about 1 mg/kg to about 20 mg/kg per day for an adult person), in a single or multiple doses. When administered in multiple doses it is typically administered from twice to four times a day.

This invention will be described with reference to Synthesis Examples of the compounds which are active ingredient of the prophylactic and therapeutic agent of this invention and Preparation Examples using the compounds.

SYNTHESIS EXAMPLE 1

A 500 ml Sakaguchi flask was charged with 100 ml of a culture medium of the following formulation, and *Stachybotrys* sp. K-76 was cultivated at 28° C. and a pH of 6 for 4 days with shaking.

| Formulation of Culture Medium | |
|---|---|
| | (%) |
| Glycerol | 0.5 |
| Starch | 1.0 |
| Lactose | 0.2 |
| Soybean Powder | 0.5 |
| Yeast Extract | 0.1 |
| Malt Extract | 0.2 |
| $CaCO_3$ | 0.3 |
| $MgSO_4$ | 0.05 |

A 30-liter jar fermentor was charged with 20 liters of a culture medium of the above formulation, and one flask of the resulting seed culture was cultivated in the culture medium at 28° C. for 5 days with stirring at 300 rpm at an aeration rate of 1 liter per liter of the culture medium per minute. The resulting culture broth was centrifuged at a speed of 8,000 rpm to remove the microbial cells. To the supernatant liquid was added 5 liters of methanol, and the mixture was stirred and then allowed to stand for 3 hours. The mixture was centrifuged and the solid material was removed. The supernatant was extracted with an equal quantity, by volume, of ethyl acetate. The solvent of the ethyl acetate layer was distilled off under reduced pressure. The residue was dissolved in methanol, and passed through a column of activated carbon. The eluate was concentrated to dryness under reduced pressure. The dried mass was dissolved in a mixture of chloroform and ethyl acetate (1:1, v/v) and gel-filtered through a column of Sephadex LH-20. The filtrate was subjected to thin-layer chromatography, using a mixture of ethyl acetate, chloroform and acetic acid (volume ratio of 50:50:2) as a developing solvent, and a fraction having an anti-complement activity corresponding to Rf=0.34 was collected. Alternatively the filtrate was subjected to thin-layer chromatography, using a mixture of benzene, butanol and acetic acid (volume ration of 60:15:5) as a developing solvent, and a fraction having an anti-complement activity corresponding to Rf=0.58 was collected. The solvent was removed from the fraction by distillation to afford 2.0 g of 6,7-dihydroxy-2,5,5,8a-tetramethyl-1,2,3,4,4a,5,6,7,8,8a-decahydronaphthalene-1-spiro-2'-(6',7'-diformyl-4'-hydroxy-2',3'-dihydrobenzofuran), a light yellow weakly acidic substance having an anti-complement activity. The compound had the following physicochemical characteristics.

(1) $[\alpha]_D^{20} = -48°$ (C=2.5, methanol)
(2) Elemental Analysis Values for $C_{23}H_{30}O_6$:
Calc'd (%): C 68.64, H 7.51
Found (%): C 68.58, H 7.55
(3) Ultraviolet Absorption Spectral (UV) Analysis $\lambda_{max}^{ethanol} = 246$ nm ($\epsilon = 16474$), 307 nm ($\epsilon = 6659$)

SYNTHESIS EXAMPLE 2

Silver nitrate (2:1 g) was dissolved in 1 ml of water, and 3.5 ml of a 5.8M aqueous solution of sodium hydroxide was added thereto. The mixture was stirred at room temperature for 20 minutes. Then, a solution of 1.0 g of 6,7-dihydroxy-2,5,5,8a-tetramethyl-1,2,3,4,4a,5,6,7,8,8a-decahydronaphthalene-1-spiro-2'-(6',7'-diformyl-4'-hydroxy-2',3'-dihydrobenzofuran) obtained as described in Synthesis Example 1 in 3 ml of ethanol was added thereto. The reaction medium was stirred at room temperature for 1.5 hours, and the pH was adjusted to about 2 with 2N hydrochloric acid. The reaction mixture was extracted with the same quantity by volume of ethyl acetate, and the solvent in the extract was distilled off under reduced pressure. The residue was purified by silical gel column chromatography [silica gel "Wako C-200", a product of Wako Junyaku Kabushiki Kaisha, chloroform/ethyl acetate/acetic acid (100:50:2 by volume) as an eluent]. A fraction corresponding tp Rf=0.37 by thin-layer chromatography using a mixture of ethyl acetate, chloroform and acetic acid in a volume ratio of 50:50:2 as a developing solvent, or a fraction corresponding to Rf=0.71 in thin-layer chromatography, using a mixture of benzene, butanol and acetic acid in a volume ratio of 60:15:5 as a developing solvent, was collected. The solvent was removed from the fraction by distillation to afford 700 mg of 4,8-dihydroxy-6-oxo-2,3,6,8-tetrahydro-furo[3,4-g]benzofuran-2-spiro-1'-(6',7'-dihydroxy-2',5',5',8'a-tetramethyl-1',2',3',4',4'a,5',6',7',8',8'a-decahydronaphthalene), as light yellow amorphous crystals. The compound had the following physicochemical properties.

(1) $[\alpha]_D^{20} = -44.8°$ (C=0.9, methanol)
(2) Elemental Analysis Values for $C_{23}H_{30}O_7$:
Calc'd (%): C66.03, H 7.18
Found (%): C 65.93, H 7.21

SYNTHESIS EXAMPLE 3

To 5 ml of a 0.4N aqueous solution of sodium hydroxide and 5 ml of ethanol was added 418 mg of 4,8-dihydroxy-6-oxo-2,3,6,8-tetrahydro-furo[3,4-g]benzofuran-2-spiro-1'-(6',7'-dihydroxy-2',5',5',8'a-tetramethyl-1',2',3',4',4'a,5',6',7',8',8'a-decahydronaphthalene). The mixture was stirred at 30° to 40° C. for 30 minutes in a stream of nitrogen. After the reaction, the solvent was distilled off under reduced pressure. The residue was dried, and 10 ml of acetone was added thereto. The acetone-soluble portion was removed by filtration. The resulting crude crystals were recrystallized from water/acetone by adding acetone dropwise to the aqueous solution until crystals precipitated to afford 342 mg of disodium 6,7-dihydroxy-2,5,5,8a-tetramethyl-1,2,3,4,4a,5,6,7,8,8a-decahydronaphthalene-1-spiro-2'-(6'-carboxylate-7'-formyl-4'-oxide-2',3'-dihydrobenzofuran) as light yellow amorphous crystals. The resulting compound had the following physicochemical properties.

(1) $[\alpha]_D^{20} = -44.2°$ (C=1.25, $H_2O$)
(2) Elemental Analysis Values for $C_{23}H_{28}O_7Na_2$:
Calc'd (%): C 59.74, H 6.10
Found (%): C59.48, H 5.91
(3) Ultraviolet Absorption Spectral (UV) Analysis $\mu_{max}^{H_2O} = 252$ nm ($\epsilon = 20500$), 330 nm ($\epsilon = 45900$)

PREPARATION EXAMPLE 1

| Compound of the invention obtained in Synthesis Example 3 | 500 mg |
| --- | --- |
| Glucose | 250 mg |
| Distilled Water for Injection | to make the total amount 5 ml |

The disodium salt of the compound obtained in Synthesis Example 3 and glucose were dissolved in distilled water for injection. The solution was poured into a 5 ml ampoule. The air was purged with nitrogen, and the ampoule was heated at 121° C. for 15 minutes to sterilize the solution, to obtain an injectable preparation.

PREPARATION EXAMPLE 2

| Compound of the invention obtained in Synthesis Example 2 | 500 mg |
| --- | --- |
| Semi-Synthetic Glyceride Base | to make the total amount 1,000 mg |

Compound of the invention obtained in Synthesis Example 2 was added to the semi-synthetic glyceride base, and they were mixed and suspended at 50° C. The mixture was cast into a mold, and allowed to cool naturally. The product was removed, and thus, a suppository was obtained.

PREPARATION EXAMPLE 3

| Compound of the invention obtained in Synthesis Example 3 | 150 g |
| --- | --- |
| Avicel (trademark for a product of Asahi Kasei Kabushiki Kaisha) | 40 g |
| Corn Starch | 30 g |
| Magnesium Stearate | 2 g |
| TC-5 (trademark for hydroxypropylmethyl cellulose, produced by Shinetsu Chemical Industry Co. Ltd.) | 10 g |
| Macrogol 6000 (polyethylene glycol having a molecular weight of about 6,000 produced by Shinetsu Chemical Industry Co., Ltd.) | 3 g |
| Castor Oil | 40 g |
| Methanol | 40 g |

Compound of the invention obtained in Synthesis Example 3, the Avicel, the corn starch and the magnesium stearate were mixed and ground, and then tableted using a conventional pounder (R 10 mm) for sugar coating (produced by Kikusui Seisakusho Co., Ltd.). The resulting tablets were coated with a film coating agent composed of TC-5 Macrogol-6000, castor oil and methanol to produce film-coated tablets.

PREPARATION EXAMPLE 4

| Compound of the invention obtained in Synthesis Example 2 | 100 g |
| --- | --- |
| Avicel | 40 g |
| Corn Starch | 30 g |
| Magnesium Stearate | 2 g |
| Methyl Acrylate/Methacrylic Acid | 5.7 g |

| | |
|---|---|
| Copolymer | |
| Triacetin | 0.6 g |
| Ethanol | 50.4 g |

Compound of the invention obtained in Synthesis Example 2, the Avicel, the corn starch and the magnesium stearate were mixed and ground, and tabletted using a pounder for sugar coating (R 10 mm). The resulting tablets were coated with a film coating agent composed of the methyl acrylate/methacrylic acid copolymer, the triacetin and the ethanol to form enteric-coated tablets.

The pharmacological activities of the prophylactic or therapeutic agent for hepatitis according to the present invention will be explained in greater detail hereinbelow.

1. Prophylactic and Therapeutic Effect

In humans, fulminant hepatitis necrosis of liver cells over a wide area of the liver is known to occur very suddenly, although no clear cause for this phenomenon has been elucidated yet, and this leads to a severe hepatic insufficiency accompanied by clouding of consciousness, etc. When these phenomena such as the above-described broad range necrosis of liver cells occur, increases in the levels of glutamic oxalacetic transaminase (hereafter "GOT") and lactic dehydrogenase (hereafter "LDH") are observed in the blood serum.

The test for evaluating the prophylactic and therapeutic effect of the compound represented by the formula (I) or (II) was conducted in accordance with the method of Mori et al., Kanzo, Vol. 17, pp. 580–589 (1976), using S.D. strain rats having a body weight of about 300 g as test animals, and causing fulminant hepatitis (Schwarzman hepatitis) to occur.

More particularly, 4 test groups, each consisting of 5 S.D. strain rats, were administered 0.1 mg/body of endotoxin (LPS: E. coli 0.26: $B_6$, a product of Difco Co.) peritoneally (by injection), and after 48 hours the same endotoxin preparation was administered by injection to each group at a dosage of 0.05, 0.2, 0.5 or 1.2 mg/body for boostering. On the other hand, 5 mg/body of the active ingredient of the agent of this invention was administered peritoneally by injection once a day for 6 days. This treatment was initiated 2 days before the first administration of endotoxin took place and ended on the day after the second administration of endotoxin for boostering. The test animals were victimized (i.e., destroyed and analyzed) 48 hours after the second administration of endotoxin, and the levels of GOT and LDH in the serum of the victimized rats were determined using a UV method described in *American Journal of Clinical Pathology*, Vol. 47, pp. 419–428 (1967) and *Cancer Research*, Vol. 14, pp. 513–515 (1954). In addition, degree of occurrence of hepatic necrosis and distribution of endotoxin in the liver were obseved microscopically using sections of liver of the victimized animals. The compound obtained in Synthesis Example 2 was used as the active ingredient. The same procedure was repeated on animals of 4 control groups which were not administered the active ingredient.

Figure 1:
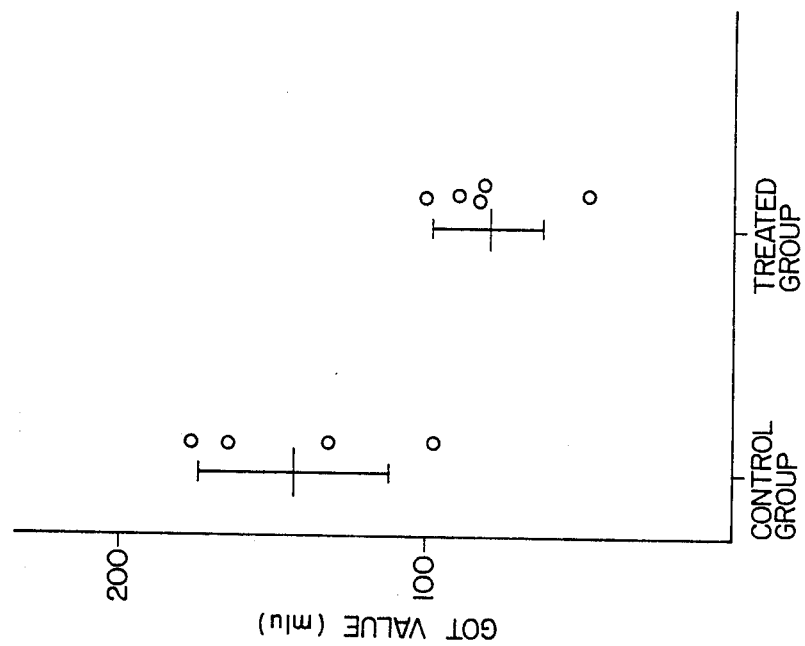
FIG. 1 illustrates levels of glutamic oxalacetic transaminase concentrations in control groups and groups treated with the composition of the invention.

The levels of GOT and of LDH in the serum determined for the group which received endotoxin boostering amount of 0.5 mg/body at the second administration and for the control group are shown in FIGS. 1 and 2, respectively. In FIGS. 1 and 2, the symbol o indicates the values obtained for each test animal in the group. Evaluation of the results was made based on the average value ± an error obtained by statistical treatment thereof.

From the results shown in FIGS. 1 and 2 it can be seen that the GOT and LDH levels in serum of the test animals belonging to the group which was received the active ingredient of this invention are significantly lower than those of the control group. This indicates that the active ingredient of this invention significantly inhibits the occurrence of fulminant hepatitis (Schwarzman hepatitis).

Figure 3B:
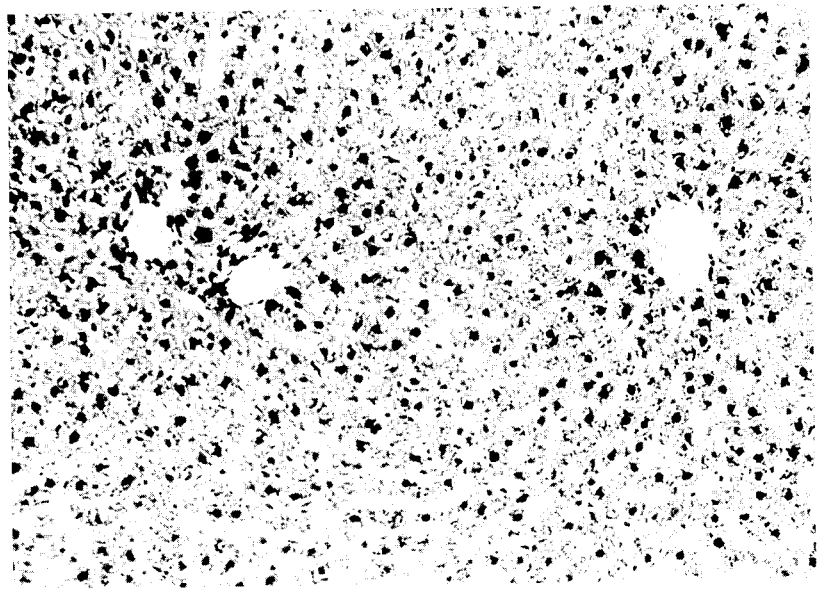
FIG. 3b is a microphotograph (magnification: ×100) of a section of liver of test animal which was administered the active ingredient of this invention.
Figure 3A:
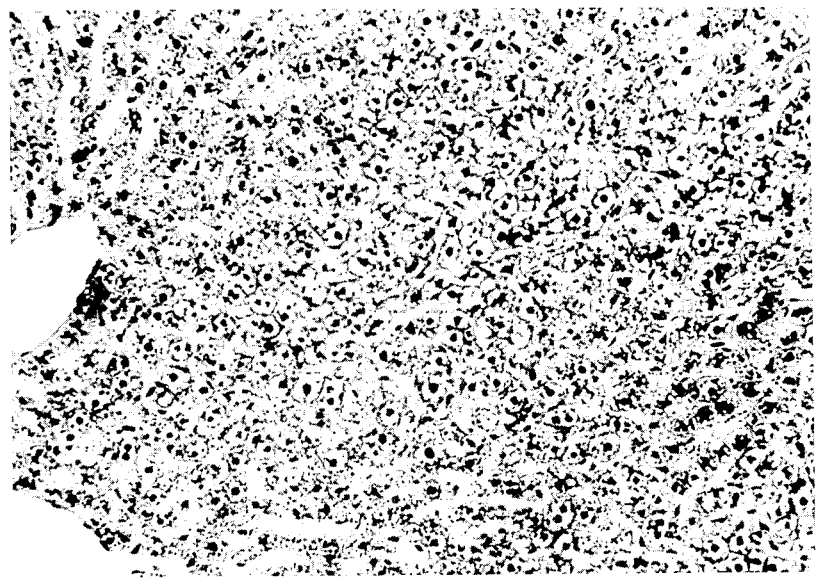
FIG. 3a is a microphotograph (magnification: ×100) of a section of liver of test animal which was not treated with the active ingredient of this invention.

Further, microscopic observation (magnification: ×100) of sections of livers of the test animals show that local necrosis and subchronic cell degeneration of liver cells were observed abundantly in the test animals of the control group (FIG. 3a), while the degree of cell degeneration was very slight, and the occurrence of damage of cells of liver was significantly inhibited or such damage was substantially cured in the test animals of the group administered with the active ingredient of this invention (FIG. 3b).

Figure 4B:
FIG. 4b is a fluorescence microphotograph (magnification: ×400) of a section of liver of test animal which was administered the active ingredient of this invention.
Figure 4A:
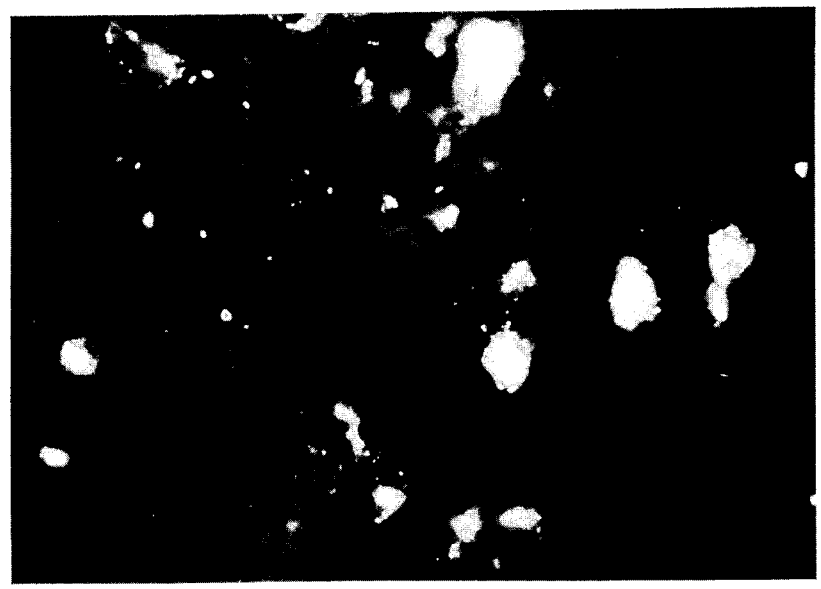
FIG. 4a is a fluorescence microphotograph (magnification: ×400) of a section of liver of test animal which was not treated with the active ingredient of this invention.

The sections of livers of the test animals of the same groups as above were observed using the fluorescence antibody method described in *Journal of Experimental Medicine*, Vol. 91, pp. 1–13 (1950). From this observation it was evident that endotoxin was distributed in Kupffer cells as well as outside these cells abundantly in the animals of the control group (FIG. 4a) while distribution of endotoxin is strongly localized in Kupffer cells but scarcely outside the cells in the liver sections of the test animals of the treated group (FIG. 4b). This also indicates that the active ingredient of this invention is effective in markedly inhibiting the occurrence of the damage causing activity on liver cells directly ascribable to endotoxin or in treating the endotoxin induced damages.

As described above, the agent of this invention is effective in the prophylaxis and therapy of fulminant hepatitis of mammals including the animals tested and humans and those serious hepatitis related thereto, such as virus hepatitis, acute hepatitis, subacute hepatitis, chronic hepatitis, etc.

2. Acute Toxicity

The acute toxicity of the compound obtained in Synthesis Example 2 was determined by administering it intravenously to rat. The $LD_{50}$ value obtained was 500 mg/kg.

3. Clinical Data

A 35 years old male human patient who had suffered acute viral hepatitis for two years and received rest treatment, dietitic treatment and medicinal treatment since the diagnosis of the disease but showed substantially no healing (although a slight improvement in certain test data of hepatic functions was observed), and who showed increases in the serum transaminase level and serum bilirubin level and complained of extreme fatigue and a feeling of loss of strength, and was therefore diagnosed to be suffering chronic hepatitis, was administered (orally) a tablet containing about 500 mg of the active ingredient of the present invention (compound prepared according to Synthesis Example 3 and dissolved in a physiological salt solution) twice a day. This treatment was continued for 2 months.

The levels of glutamic oxalacetic transaminase (GOT), glutamic pyruvic transaminase (GPT) and serum bilirubin (SB) were determined according to the conventional methods described in *Am. J. Clin. Path.*, 28, 56–63 (1957) (for GOT and GPT) and in *J. Biol. Chem.*, 119, 481–490 (1937) (for SB), and compared with the data obtained before the administration, as shown in Table below.

TABLE

|  | GOT (unit) | GPT (unit) | SB (mg/dl) |
| --- | --- | --- | --- |
| Before Administration | 180 | 143 | 2.6 |
| After Administration (2 months) | 45 | 67 | 1.5 |

Furthermore, the patient described considerably improved feeling with respect to fatigue and loss of strength.

While the invention has been described in detail and with reference to specific embodiments thereof, it will be apparent to one skilled in the art that various changes and modifications can be made therein without departing from the spirit and scope thereof.

Industrial Applicability

As described in the foregoing, the agent of this invention exhibits excellent prophylactic and therapeutic effects for hepatitis.

What is claimed is:

1. A method for treating hepatitis in a mammal comprising administering to said mammal an effective amount of a sesquiterpene compound represented by the formula (I) or (II)

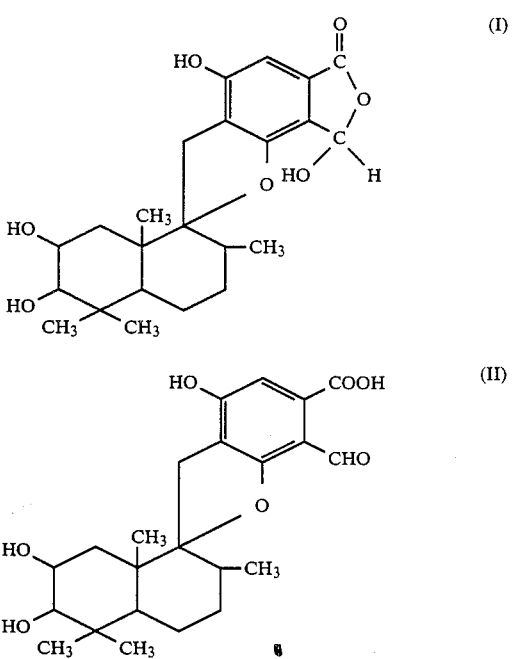

or a pharmaceutically acceptable salt thereof.

2. A method as in claim 1, wherein said compound is administered at a daily dosage of from 1 mg to 20 mg/kg body weight.

* * * * *